United States Patent [19]

Goethert

[11] Patent Number: 4,837,792

[45] Date of Patent: Jun. 6, 1989

[54] COMPUTER TOMOGRAPHY APPARATUS

[75] Inventor: Dieter Goethert, Leutenbach, Fed. Rep. of Germany

[73] Assignee: Siemens Aktiengesellschaft, Berlin and Munich, Fed. Rep. of Germany

[21] Appl. No.: 167,084

[22] Filed: Mar. 11, 1988

[30] Foreign Application Priority Data

Mar. 20, 1987 [DE] Fed. Rep. of Germany ... 8704182[U]

[51] Int. Cl.$^4$ .............................................. G03B 41/16
[52] U.S. Cl. ......................................... 378/4; 378/11; 378/138
[58] Field of Search ................. 378/4, 11, 19, 20, 121, 378/138, 207

[56] References Cited

U.S. PATENT DOCUMENTS 4,220,860 9/1980 Carlson et al. .
4,457,009 6/1984 Botden ................................. 378/19
4,559,639 12/1985 Glover et al. .

FOREIGN PATENT DOCUMENTS 55-159596 12/1980 Japan .
57-21100 2/1982 Japan .

Primary Examiner—Carolyn E. Fields
Assistant Examiner—David P. Porta
Attorney, Agent, or Firm—Hill, Van Santen, Steadman & Simpson

[57] ABSTRACT

A computer tomography apparatus has an x-ray source which is fed with a high voltage supply. Operation of the x-ray source over an extended period of time causes the focal spot on the anode to change position, thereby degrading the image which is constructed from the series of exposures, because construction of the image is based in part upon the focus being at a known position. A focus position computer is therefore provided which receives signals from the high voltage supply corresponding to the operating parameters of the x-ray source. Based on a known relationship between these parameters, the length of operating time, and the expected position of the focus, the focus position computer calculates the expected change in position of the focus, and supplies a signal corresponding to this change to the image construction computer, which takes the change in focus position into account in constructing the image for display.

2 Claims, 1 Drawing Sheet

COMPUTER TOMOGRAPHY APPARATUS

BACKGROUND OF THE INVENTION

1. Field of the Invention

The present invention is directed to a computer tomography apparatus, and in particular to such an apparatus including means for identifying a change in the focus position of the x-ray beam and means for taking this change into account in constructing the image for display.

2. Description of the Prior Art

Computer tomography devices are known which generally include a measuring unit having an x-ray source and a radiation receiver. The x-ray source emits a fan-shaped radiation beam in which a patient is disposed, with the radiation attenuated by the patient being incident on a radiation receiver consisting of a row of individual detectors. Each detector forms an electrical signal corresponding to the radiation intensity incident thereon. The x-ray source and radiation detector are rotated around the patient for transirradiating a measuring field from different directions. The output signals from the individual detectors at the different transirradiation directions are supplied to a computer which constructs an image therefrom for visual display.

In computer tomography devices of this type, a condition for obtaining an image free of artifacts is that the focus be at a predetermined known position with respect to the radiation receiver. In practice, however, the focus will migrate or change position slightly relative to the known or rated position, particularly in the longitudinal direction of the patient support (z-direction). This is primarily due to heating of the x-ray tube, in particular the anode thereof, during use.

One proposed solution to compensate for such changes in focus position is described in U.S. Pat. No. 4,559,639, wherein a plurality of detectors are provided to measure the change in focus position by direct sensing thereof.

SUMMARY OF THE INVENTION

It is an object of the present invention to provide a computer tomography apparatus of the type described above wherein a correction for the change of the focus position can be undertaken without the need for direct measurement thereof, thus eliminating the need for the presence of measuring detectors.

The above object is achieved in accordance with the principles of the present invention in a computer tomography apparatus wherein a focus position computer is provided which receives signals from the high voltage supply which feeds the x-ray source. The signals from the high voltage supply identify the operating values for the x-ray source, such as voltage, current and duration of use. From these values, the temperature of the rotating anode of the x-ray source can be calculated, and a known functional relationship exists between this operating temperature and the focus position at any given time, particularly in the z-direction. The focus position computer accordingly generates a signal identifying the current position of the focus, and supplies this signal to the image construction computer. The image construction computer takes the change of focus position into account in constructing the image for visual display. The resulting image is thus free of image artifacts caused by the assumption that the position of the focus is unchanged.

The functional relationship between the temperature which is calculated from the operating values of the high voltage supply and the position of the focus in the z-direction is measured once for a typical arrangement, and is stored in the focus position computer.

DESCRIPTION OF THE PREFERRED EMBODIMENTS

Figure 1:
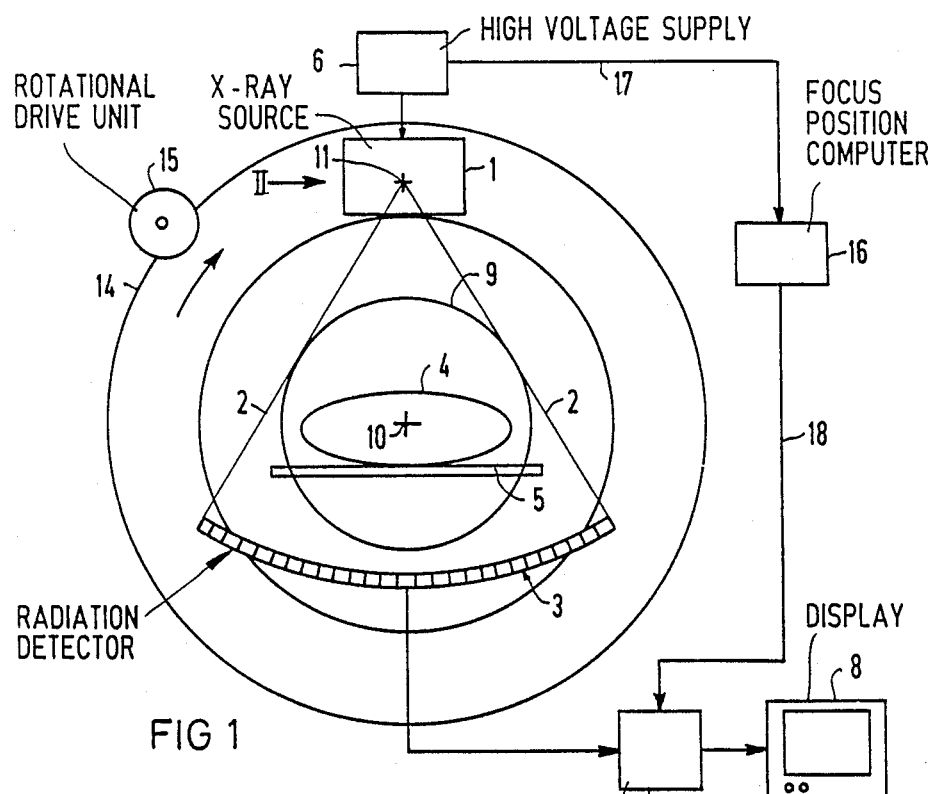
FIG. 1 is a schematic view of a computer tomography apparatus constructed in accordance with the principles of the present invention.

The basic components of a computer tomography apparatus constructed in accordance with the principles of the present invention are schematically shown in FIG. 1. The apparatus includes a measuring unit consisting of an x-ray source 1 which emits a fan-shaped x-ray beam 2 and a radiation receiver 3, which consists of a row of individual detectors, for example, 512 individual detectors. A patient 4 to be examined rests on a patient support table 5. For scanning the patient 4, the measuring unit consisting of the x-ray source 1 and the radiation receiver 3 is rotated through 360° around a measuring field 9 in which the patient 4 is disposed. The rotational axis is referenced at 10. The x-ray source 1 is fed by a high voltage supply 6, and may be pulsed or continuously operated. Given predetermined angular positions of the x-ray source 1 and the radiation detector 3, sets of data are generated which are supplied from the receiver 3 to an image construction computer 7, which calculates the attenuation coefficients of predetermined picture elements from the generated data sets, and provides a pictorial reproduction of a slice of the patient 4 on a display 8.

The change in the direction of the x-ray beam 2 is achieved by rotating a live ring 14, on which the x-ray source 1 and the radiation receiver 3 are mounted, by a rotational drive unit 15.

Figure 2:
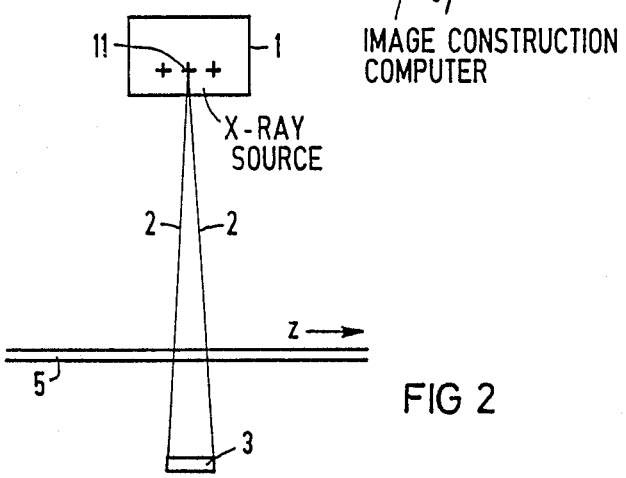
FIG. 2 is a schematic view taken in the direction of the arrow indicated at II in FIG. 1 for explaining the operation of the invention.

As shown in FIG. 2, the focus 11 of the x-ray source 1 can migrate or change position slightly in the z-direction during operation due to heating of the x-ray source 1, particularly the anode thereof. A fixed functional relationship between the various focus positions and the temperature of the x-ray source 1, particularly the rotating anode thereof, is established for a specific computer tomography apparatus. This functional relationship is stored in a focus position computer 16. The focus position computer 16 receives input signals on a line 17 from the high voltage supply 6 identifying various operating values of the x-ray source 1. From the signals supplied on line 17, the focus position computer 16 calculates the current temperature of the x-ray source 1, and using the aforementioned fixed relationship then calculates the respective focus position from the calculated temperature. A signal corresponding to the current focus position is supplied form the focus position computer 16 to the image construction computer 7 on line 18. The image construction computer 7 can then replace the known or rated position of the focus 11 with the updated focus position obtained from the focus position computer 16, or undertake any suitable correction instead of making an actual substitution, in constructing the image for display. The image on the display 8 is thus free of artifacts whch would otherwise be caused by changes in the focus position due to heating of the x-ray source 1.

Although modifications and changes may be suggested by those skilled in the art it is the intention of the inventor to embody within the patent warranted hereon all changes and modifications as reasonably and properly come within the scope of his contribution to the art.

I claim as my invention:

1. A computer tomography apparatus for obtaining a tomograph of an examination subject, said apparatus comprising:

means for generating an x-ray beam emanating from a focus, said focus changing position over time due to heating of said means for generating an x-ray beam during operation;

a radiation receiver disposed for receiving radiation from said x-ray beam attenuated by said examination subject and for generating a plurality of electrical signals corresponding to the received radiation intensity;

means for rotating said means for generating an x-ray beam and said radiation receiver around said examination subject to irradiate said examination subject from different directions thereby generating a plurality of data sets from said electrical signals of said radiation receiver;

image construction means for calculating an image of a slice of said examination subject from said data sets using the position of said focus in said means for generating an x-ray beam;

means for feeding said means for generating an x-ray beam with operating values, and for generating electrical signals corresponding to said operating values; and means to which said electrical signals corresponding to said operating values are supplied for calculating the temperature of said means for generating an x-ray beam therefrom and for calculating the position of said focus in said means for generating an x-ray beam based on the calculated temperature and for supplying a signal corresponding to the position of said focus to said means for constructiong an image for use by said image construction means in calculating said image.

2. A computer tomography apparatus as claimed in claim 1, further comprising means for visually displaying the image constructed by said image construction means.

* * * * *